(12) United States Patent
Bogaart et al.

(10) Patent No.: US 9,835,954 B2
(45) Date of Patent: Dec. 5, 2017

(54) INSPECTION METHOD AND APPARATUS, SUBSTRATES FOR USE THEREIN AND DEVICE MANUFACTURING METHOD

(71) Applicant: ASML Netherlands B.V., Veldhoven (NL)

(72) Inventors: Erik Willem Bogaart, Eindhoven (NL); Franciscus Godefridus Casper Bijnen, Valkenswaard (NL); Arie Jeffrey Den Boef, Waalre (NL); Simon Gijsbert Josephus Mathijssen, Den Bosch (NL)

(73) Assignee: ASML Netherlands B.V., Veldhoven (NL)

( * ) Notice: Subject to any disclaimer, the term of this patent is extended or adjusted under 35 U.S.C. 154(b) by 11 days.

(21) Appl. No.: 14/892,880

(22) PCT Filed: May 2, 2014

(86) PCT No.: PCT/EP2014/058996
§ 371 (c)(1),
(2) Date: Nov. 20, 2015

(87) PCT Pub. No.: WO2014/187656
PCT Pub. Date: Nov. 27, 2014

(65) Prior Publication Data
US 2016/0097983 A1    Apr. 7, 2016

Related U.S. Application Data

(60) Provisional application No. 61/825,651, filed on May 21, 2013.

(51) Int. Cl.
*G03F 7/00*     (2006.01)
*G01N 21/95*    (2006.01)
(Continued)

(52) U.S. Cl.
CPC ..... *G03F 7/70483* (2013.01); *G01N 21/9501* (2013.01); *G01N 21/956* (2013.01); *G03F 7/70625* (2013.01); *G01N 2021/656* (2013.01)

(58) Field of Classification Search
CPC ......... G01N 2021/656; G01N 21/9501; G01N 21/956; G03F 7/70483; G03F 7/70625
See application file for complete search history.

(56) References Cited

U.S. PATENT DOCUMENTS 4,047,029 A * 9/1977 Allport .................. G01N 23/16
                                                      162/263
4,458,994 A    7/1984 Jain et al.
(Continued)

FOREIGN PATENT DOCUMENTS

CN         1685217 A      10/2005
CN         1969215 A       5/2007
WO    WO 2013/025224 A1    2/2013

OTHER PUBLICATIONS

International Search Report directed to related International Patent Application No. PCT/EP2014/058996, dated Jun. 23, 2014; 4 pages.
(Continued)

*Primary Examiner* — Mark R Gaworecki
(74) *Attorney, Agent, or Firm* — Sterne, Kessler, Goldstein & Fox P.L.L.C.

(57) ABSTRACT

A substrate is provided with device structures and metrology structures (800). The device structures include materials exhibiting inelastic scattering of excitation radiation of one or more wavelengths. The device structures include structures small enough in one or more dimensions that the characteristics of the inelastic scattering are influenced significantly by quantum confinement. The metrology structures (800) include device-like structures (800*b*) similar in composition and dimensions to the device features, and calibration structures (800*a*). The calibration structures are (Continued)

similar to the device features in composition but different in at least one dimension. Using an inspection apparatus and method implementing Raman spectroscopy, the dimensions of the device-like structures can be measured by comparing spectral features of radiation scattered inelastically from the device-like structure and the calibration structure.

17 Claims, 7 Drawing Sheets

(51) Int. Cl.
  *G03F 7/20* (2006.01)
  *G01N 21/956* (2006.01)
  *G01N 21/65* (2006.01)

(56) References Cited

U.S. PATENT DOCUMENTS

| | | | |
|---|---|---|---|
| 6,498,801 | B1 | 12/2002 | Dudelzak et al. |
| 6,657,708 | B1 | 12/2003 | Drevillon et al. |
| 6,986,280 | B2 | 1/2006 | Muckenhirm |
| 7,433,056 | B1 | 10/2008 | Janik |
| 7,473,917 | B2 | 1/2009 | Singh |
| 7,595,973 | B1 * | 9/2009 | Lee .................. H01G 4/005 361/303 |
| 7,903,260 | B1 | 3/2011 | Janik |
| 2007/0252984 | A1 | 11/2007 | Van Beek et al. |
| 2007/0285643 | A1 | 12/2007 | Wedowski et al. |
| 2011/0081003 | A1 * | 4/2011 | Harding ........... G01N 23/20066 378/88 |
| 2012/0028376 | A1 * | 2/2012 | Radwan ............ H01L 21/76802 438/5 |
| 2012/0034686 | A1 | 2/2012 | Berlin et al. |

OTHER PUBLICATIONS

International Preliminary Report on Patentability and Written Opinion of the International Searching Authority directed to related International Patent Application No. PCT/EP2014/058996, dated Nov. 24, 2015; 8 pages.
Volodin, et al., "Improved Model of Optical Phonon Confinement in Silicon Nanocrystals," Journal of Experimental and Theoretical Physics, vol. 116, No. 1 (Jan. 2013); pp. 100-108.
Paillard, et al., "Improved one-phonon confinement model for an accurate size determination of silicon nanocrystals," Journal of Applied Physics, vol. 86, No. 4 (Aug. 15, 1999); pp. 1921-1924.
Roodenko, et al., "Modified phonon confinement model for Raman spectroscopy of nanostractured materials," Physical Review B, vol. 82, No. 11 (Sep. 1, 2010); pp. 115210-1-115210-11.
Faraci, et al., "Modified Raman confinement model for Si nanocrystals," Physical Review B, vol. 73 (Jan. 10, 2006); pp. 033307-1-033307-4.
Faraci, et al., "Quantum size effects in Raman spectra of Si nanocrystals," Journal of Applied Physics, vol. 109 (Apr. 7, 2011); 074311-1-0743211-4.
Sze, et al., Physics of Semiconductor Devices, Third Edition, Hoboken, NJ: John Wiley & Sons, Inc. (2007); p. 61.
"Exciton," Wikipedia, accessible at http://en.wikipedia.org/wiki/Exciton (accessed May 2, 2013); 4 pages.
"Raman spectroscopy," Wikipedia, accessible at http://en.wikipedia.org/wiki/Raman_spectroscopy (accessed May 2, 2013); 8 pages.
Zhao, et al., "Quantum Confinement and Electronic Properties of Silicon Nanowires," Physical Review Letters, vol. 92, No. 23 (Jun. 11, 2004); pp. 236805-1-236805-4.
Wang, et al., "Raman spectral study of silicon nanowires: High-order scattering and phonon confinement effects," Physical Review B, vol. 61, No. 24 (Jun. 15, 2000); pp. 16828-16832.
Greetham, et al., "Femtosecond stimulated Raman scattering: development of a new facility for high temporal resolution Raman spectroscopy," Central Laser Facility Annual Report 2006-2007, Rutherford Appleton Laboratory, Harwell Science & Innovation Campus; pp. 181-184.

* cited by examiner

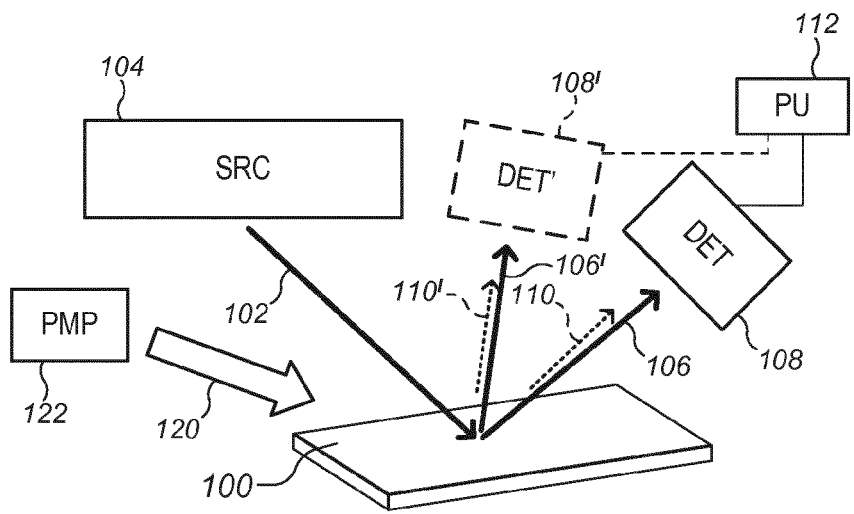
Fig. 3
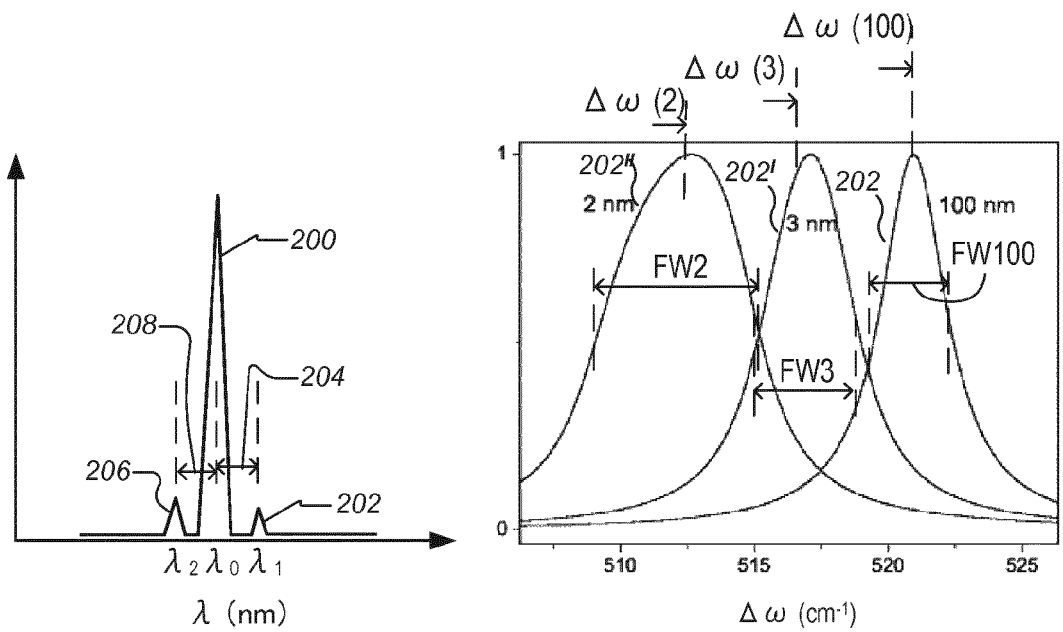
Fig. 4
Fig. 5

INSPECTION METHOD AND APPARATUS, SUBSTRATES FOR USE THEREIN AND DEVICE MANUFACTURING METHOD

CROSS-REFERENCE TO RELATED APPLICATIONS

This application claims the benefit of U.S. provisional application 61/825,651, which was filed on May 21, 2013 and which is incorporated herein in its entirety by reference.

FIELD

The present invention relates to apparatus and methods of inspection usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer).

Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical dimension (typically linewidth) of developed photosensitive resist and/or etched product features. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

As the resolution of lithographic processes increases, ever smaller features will created on substrates, below the resolution of current scatterometers. In order to perform scatterometry at higher resolution one can consider using to use shorter wavelengths of radiation. Wavelengths in the ultraviolet (UV) range may be effective for this in principle. However, optical systems for such wavelengths become particularly complex, and feature sizes continue to shrink beyond the resolution of classical optics. Technology roadmaps point to feature sizes smaller than 20 nm, and even smaller than 10 nm in coming years.

While techniques such as scanning electron microscopy (SEM) and atomic force microscopy (AFM) exist for accurate imaging of even such small features, they are contact-based methods, too slow and costly to be used as a routine inspection tool in mass-production. There is accordingly a desire for new forms of inspection methods and apparatus, particularly ones suitable for measuring mass-produced metrology targets with feature sizes at the resolution of current and next-generation lithographic processes. Ideally, a new inspection method would operate at high-speed and in a non-contact manner, to perform a role similar to that played by scatterometers used in mass-production today.

Raman spectroscopy is a technique known for measuring material characteristics, based on the phenomenon of inelastic scattering. Briefly, the Raman spectrum includes components at wavelengths shifted from the wavelength of an incident radiation beam. The change in wavelength is not caused by any fluorescence effect, but is caused by an exchange of energy between the scattered photons and the material by which it is scattered.

Typically the exchange of energy comprises coupling between the photons and vibrational energy modes of the material's molecules or lattice structure. In U.S. Pat. No. 7,903, 260 a spectroscopic scatterometer is combined with a Raman spectrometer in order to analyze material properties selectively. That is to say, US'260 teaches that, by measuring the Raman spectrum of a signal which is a first order diffraction signal from a periodic grating structure having product-like features, it can be ensured that the Raman spectrum represents the material characteristics of the product-like features. US'260 does not, however, propose any application to products smaller than the resolution of the scatterometer. Nor does it propose using the Raman spectrum as a means to investigate dimensional characteristics of a structure, as opposed to material characteristics.

SUMMARY

The present inventors have noted that, at very small dimensions, quantum effects have a strong influence on the inelastic scattering represented in the Raman spectrum, in samples subject to spatial confinement below a certain size. The inventors have further recognized that this influence of spatial confinement can be measured in Raman spectra and used as a basis to calculate dimensional characteristics of the structure, and not only material characteristics.

According to first aspect of the present invention, there is provided a method of inspecting a target structure comprising the steps of:
(a) directing radiation with a first wavelength at the target structure;
(b) receiving radiation scattered by the target and forming a spectrum of the scattered radiation so as to distinguish one or more spectral components in the spectrum having wavelengths different from the first wavelength due to inelastic scattering by the target structure;

(c) calculating a dimensional characteristic of the structure based on characteristics of said spectral components.

The method may further comprise directing pumping radiation to said target structure in addition to the radiation of the first wavelength, whereby the intensity of the spectral components used in said calculation is increased.

In particular embodiments of the invention, said processor is arranged to perform said calculation by comparing characteristics of said spectral components obtained from the target structure with characteristics of corresponding spectral components obtained from a calibration structure, the two structures being similar in all characteristics except dimension. The calibration structure may for example be larger in said critical dimension than the target structure.

Said calculation may be based on a shift in a wavelength of one or more of said spectral components and/or on a broadening of one or more of said spectral components.

The invention further provides an inspection apparatus comprising:
  illumination optics for directing radiation with a first wavelength at a target structure;
  detection optics for receiving radiation scattered by the target and for forming a spectrum of the scattered radiation;
  a detector for converting the spectrum into electrical signals, and
  a processor for calculating a dimensional characteristic of the structure based on characteristics of one or more spectral components in the detected spectrum having wavelengths different from the first wavelength.

The invention further provides a method of performing a lithographic process comprising the steps of:
  forming device structures and at least one metrology target structures on a substrate by said lithographic process,
  measuring a dimensional characteristic of said metrology target structure by a method according to the invention as set forth above; and
  controlling subsequent processing of the measured substrate and/or further substrates in accordance with the measured value of said dimensional characteristic.

In an example application, subsequent processing of the measured substrate is controlled so as to cause re-work or rejection of the substrate if the measured characteristic is outside a certain tolerance.

In another example application, processing of further substrates is controlled so as to correct a deviation observed in the dimensional characteristic calculated for the measured substrate.

The invention yet further provides a method of manufacturing a device comprising applying one or more device patterns to a substrate by a lithographic process according to the invention as set forth above and processing the substrate to form devices including said device structures as functional elements.

The invention further provides a computer program product in the form of a transient or non-transient storage medium carrying machine-readable instructions which when executed by a processing implement the invention in one or more of the above aspects. The processor may be a stand-alone processing device or it may comprise a control processor of an inspection apparatus or of a lithographic apparatus.

The invention yet further provides a substrate for use in the method and apparatus according to the invention as set forth above.

The substrate may be provided with device structures and metrology structures, the device structures including materials exhibiting inelastic scattering of excitation radiation of one or more wavelengths, the device structures including structures small enough in one or more dimensions that said characteristics of said inelastic scattering are influenced significantly by quantum confinement, the metrology structures including at least one device-like structure, being a structure similar in its composition and dimensions to the device features, and at least one calibration structure, the calibration structure being similar to the device features in its composition but different in at least one dimension.

The calibration structure may be larger than the device-like structure. The calibration structure may be large enough in one or more dimensions that the characteristics of said inelastic scattering are not significantly influenced but said quantum confinement effects. Example dimensions will depend on the material. By comparing the inelastic scattering of such structures, the substrate allows the influence of quantum confinement to be observed, and consequently allows an estimate of dimension of the device-like structure. When made of silicon, for example, the target structure may have a critical dimension, less than 22 nm, while said calibration structure has a greater than 25 nm.

The substrate may comprise an intermediate stage in the manufacture of a function device, or it may comprise a completed functional device in which the metrology structures remain.

The invention yet further provides a patterning device for use in a lithographic process, the patterning device carrying a pattern which, when applied to a substrate and subject to one or more further process steps, produces a substrate according to the invention as set forth above.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which:

FIG. 3 illustrates principle components of an inspection apparatus performing Raman spectroscopy;
FIG. 4 illustrates the phenomenon of Raman shift in spectroscopy;
FIG. 5 shows variations in a Raman spectrum, caused by dimensional confinement.

DETAILED DESCRIPTION OF EXEMPLARY EMBODIMENTS

This specification discloses one or more embodiments that incorporate the features of this present invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in a combination of hardware, firmware and.or, software. Embodiments of the present invention may also be implemented partly as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
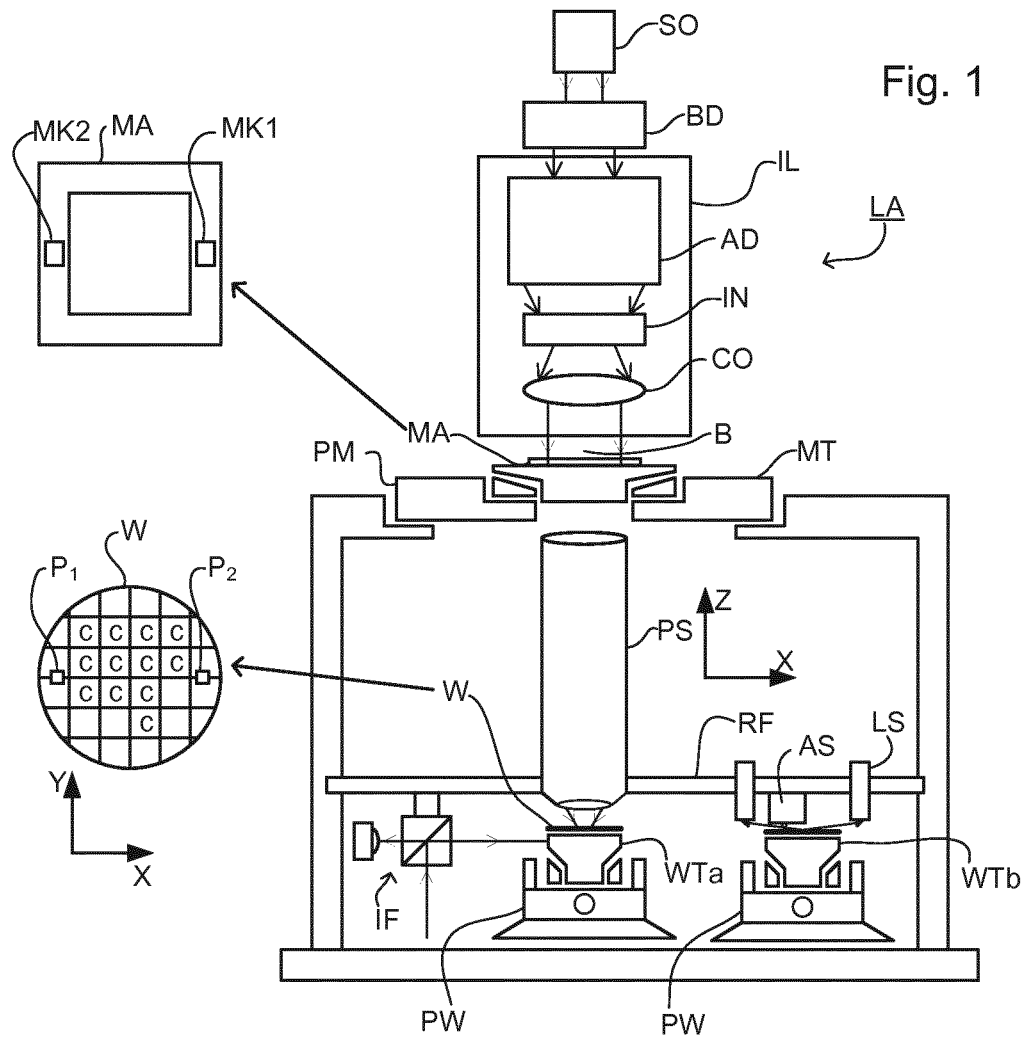
FIG. 1 depicts a lithographic apparatus.

FIG. 1 schematically shows a lithographic apparatus LAP including a source collector module SO according to an embodiment of the present invention. The apparatus comprises: an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist-coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks MK1, MK2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
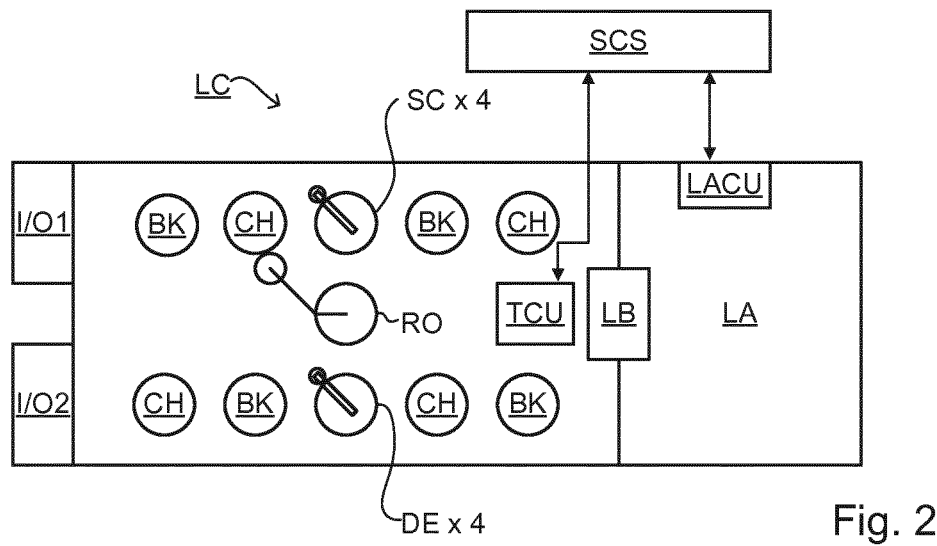
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus (not shown in FIG. 2) is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Current scatterometers are limited in their resolving power, while the semiconductor industry is moving towards technology "nodes" in which features will be below the resolving power of current scatterometers. While techniques such as scanning electron microscopy (SEM) and atomic force microscopy (AFM) are well known and able to produce images of the smallest possible structures, SEM and AFM are known also to be costly and time-consuming techniques. The attraction of the scatterometers is used for inspection in high-volume production environments is that measurements can be made relatively rapidly, that will give information about the size of structures formed, without physically inspecting each structure using SEM or AFM. The resolution of scatterometers can be extended downwards by moving to use of shorter wavelengths, such as UV radiation. However, this brings technological challenges of its own, and can only postpone the day when classical diffraction optics can no longer resolve the structures being manufactured. Consequently, we seek an instrument to perform the function presently performed by scatterometry, to characterize the dimensions of structures that are substantially smaller than the resolving power of classical optics.

FIG. 3 illustrates the basic structure and principles of operation of a Raman spectrometer, that may be used as an inspection apparatus to measure dimensional characteristics of smaller microscopic structures, according to the novel method proposed herein. A target structure 100 is irradiated by a beam of radiation 102 from a source 104. Radiation 106 scattered by the target is detected by a detection arrangement 108. As described so far, the apparatus looks similar to a conventional scatterometer, in which diffraction effects influencing the scattered radiation would be used as a basis of measurement. The novel inspection apparatus therefore exploits a phenomenon known as inelastic scattering, whereby the scattered radiation 106 contains radiation of one or more wavelengths (frequencies) that were not present in the incident radiation 102. These components are the ones analyzed in Raman spectroscopy.

The mechanism of inelastic scattering is one in which an incoming photon is scattered by the material of a sample, while gaining or losing a part of its energy to a some other form of energy within the material. Most commonly, energy from the photon is exchanged with vibrational modes of the material, such as molecular vibrations and lattice vibrations). In a periodic lattice material, vibrational modes are often considered as quasiparticles called phonons. These vibrational energy states typically have energies corresponding to photon energies in the infrared range, somewhat lower than the energy of the photons in the exciting radiation. Another type of quasiparticle that may arise, particularly in semi-conductor materials but also in insulators, is the exciton, which comprises an electron-hole pair, behaving together as a quasiparticle.

As mentioned, the phenomenon of inelastic scattering gives rise to a spectrum of scattered radiation that contains additional, shifted peaks alongside the peak at the wavelength of the incoming excitation radiation. This Raman spectrum can be analyzed and/or compared to the spectrum of known materials to obtain information on the material composition and other material properties of the sample. Where the exciting photon loses energy to the material, the scattered photon has a lower energy (longer wavelength) and this phenomenon is referred to as Stokes shift. Where the photon gains energy in the scattering, the scattered photon has a shorter wavelength, and this is known as anti-Stokes shift.

In order to enhance an inelastic scattering signal, it is known to provide a "pumping" radiation 120 from a pumping source 122. The pumping radiation is radiation suitable to change the populations of the energy states (vibrational modes, excitons or the like) that are available for interaction with the incoming radiation 102 of the Raman spectrometer. Incoming beam 102 may be referred to as the "probe" beam while the radiation 120 from the pump source 122 may be referred to as the pump beam. The excitation sources for the probe and pump beams can be lasers of the continuous wave (CW) or pulsed type, or even a combination.

To perform Raman spectroscopy, the exciting radiation 102 is typically of very narrow bandwidth, ideally comprising only a signal wavelength of radiation. In the detection arrangement, all radiation of that wavelength is filtered out prior to detection, so that the shifted wavelengths of the inelastically scattered radiation 110 can be detected, in both the wavelength and intensity. While the source 104 could, for example, be a single-wavelength laser, it would also be useful for the source to provide radiation 102 switchable between different wavelengths, in order to probe different material properties.

Signals for detection arrangements 108, 108' are digitized and used in calculations within a processing unit 112. The same instrument may also include components needed to perform conventional scatterometry, and some of the optical components such as an objective lens may be shared between these uses. Referring to the schematic example of FIG. 3, for example, one can envisage providing a metrology target that includes a grating structure, as in the known scatterometry targets. In that case, second detector 108' may be provided for the detection of radiation diffracted at non-zero order by the grating structure on the target 100.

FIG. 4 illustrates a small section of the spectrum of the scattered radiation 106/110 detected the inspection apparatus of FIG. 3. The spectrum shown in the graph of FIG. 4 represents what might be seen by detection arrangement 108. The vertical axis represents radiation intensity, in arbitrary units, while the horizontal axis represents wavelength. Suppose the exciting radiation 102 has a wavelength λ0. As would be expected, normal, elastic scattering of the incoming probe beam 102 results in large peak 200 at the wavelength λ0. On the other hand, due to coupling between the scattered photons and vibrational or other energy states in the material of the target 100, a small peak 202 appears in the spectrum at a shifted wavelength λ1. This Raman peak, as illustrated, has a longer wavelength, and consequently lower energy, than λ0. The difference in wavelengths labeled 204 is called the Raman shift, or in this case also the Stokes shift. Such a peak, of which there may be several in a real Raman spectrum, indicates that a proportion of scattered photons have lost part of their energy to a particular energy states in the material.

Because the Stokes shift 204 is to a longer wavelength, it is common in the field to refer to this Stokes shift as a "red shift" phenomenon. As also illustrated in FIG. 4, one or more second peaks 206 may appear at a wavelength λ2 that is shorter than the probe beam wavelength λ0. The Raman shift 208, also referred to as the anti-Stokes shift, may therefore be referred to as a "blue shift". References to red shift and blue shift indicate merely a shift of the radiation to longer or shorter wavelengths, respectively, and do not indicate that the wavelengths involved are in any particular part of the visible radiation spectrum. Indeed, they may be in any part of the optical spectrum, for example from infra-red, through visible spectrum and into ultra-violet wavelengths.

While in Raman spectroscopy conventionally one uses the additional spectral components to investigate material properties a target, the inventors have realized that confinement effects allow Raman spectroscopy to be used to measure dimensional properties of the materials under inspection. This potential will now be explained with reference to FIGS. 5 and 6.

In Raman spectroscopy, it is common to express the shifts 204 and 208 in terms of wave number, rather than wavelength or frequency. The wave number is the reciprocal of the wavelength, and has commonly been expressed in units of inverse centimeters ($cm^{-1}$). Raman shift $\Delta\omega$ is the most common expression, and is calculated from the original and shifted wavelengths by the following formula:

$$\Delta\omega = \left(\frac{1}{\lambda_0} - \frac{1}{\lambda_1}\right)$$

where $\Delta\omega$ is the Raman shift expressed in wavenumber, $\lambda_0$ is the excitation (probe) beam wavelength, and $\lambda_1$ is the wavelength of a feature on the Raman spectrum. Most commonly, the units shown for expressing the wavenumber in Raman spectra is inverse centimeters ($cm^{-1}$). Since wavelength signals is often expressed in units of nanometers, a scale factor of $10^7$ can be included in the right hand side of the above equation for practical purposes. The value $\Delta\omega$ will be positive in the case of a Stokes (red) shift, and negative in case of an anti-Stokes (blue) shift. One may quantify the inelastic scattering in terms of the wave vector $\underline{k}$ and frequency ω of the incoming electromagnetic field. A lattice displacement (for example) can be described by a phonon wave vector $\underline{q}$. The so called Stokes wave has the shifted wave vector $\underline{k}_{Stokes}=\underline{k}-\underline{q}$ and a shifted frequency $\omega_{Stokes}=\omega-\omega_0$. The anti-Stokes wave is defined by $\underline{k}_{anti-Stokes}=\underline{k}+\underline{q}$, and $\omega_{anti-Stokes}=\omega+\omega_0$.

The graph of FIG. 5 is reproduced from Faraci et al (2006), mentioned further below. It shows how a peak 202 occurring in the Raman spectrum of a certain material (in this case silicon) appears with a slightly different position and shape, depending on dimensional characteristics of the structure under inspection. The Raman shift $\Delta\omega$ for the peak 202 has a first value for structures with a characteristic dimension of 100 nm (curve 202), but becomes progressively less red shifted for structures with dimensions of 3 nm (202') and 2 nm (202"). Furthermore, the peaks become progressively more spread out, as represented by their full width at half maximum, marked on the graph as FW100, FW3 and FW2.

Figure 6:
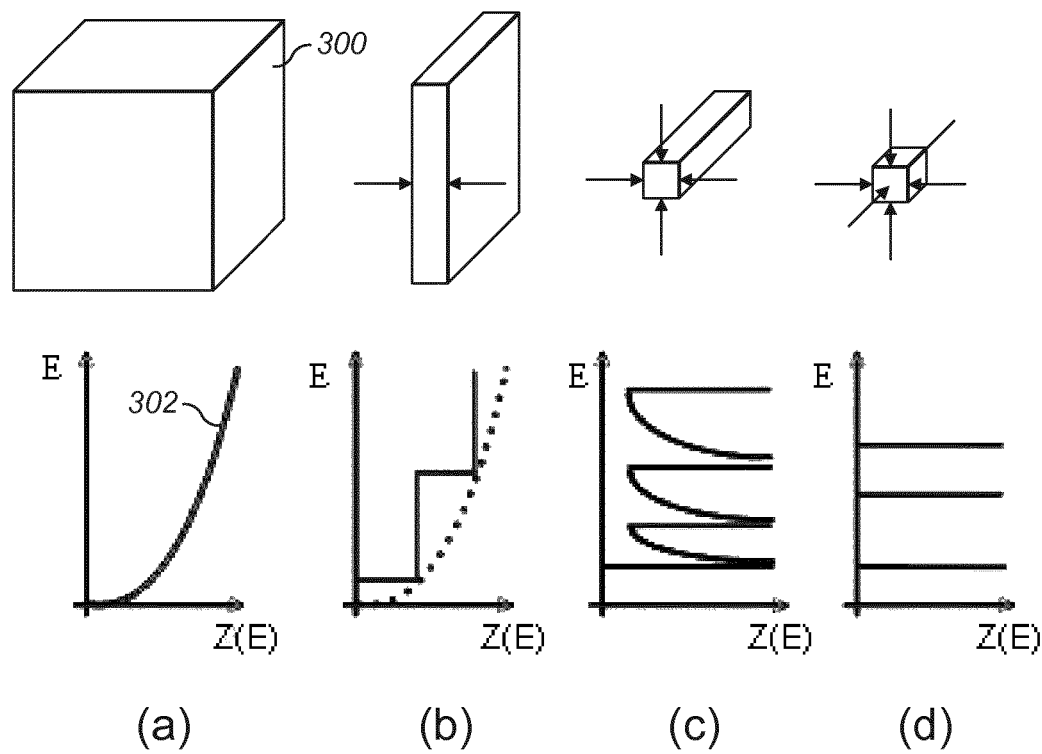
FIG. 6 (a) to (d) illustrates how the density of energy states is influenced by different types of confinement leading to phenomena illustrated in FIG. 5.

FIG. 6 illustrates the influence of spatial confinement on the density of energy states in an example material. FIG. 6(a) shows in the top part a conventional bulk material 300. Curve 302 in the graph below illustrates the density of energy states D(E) which basically has a continuous form.

FIG. 6(b) illustrates the change in the density of states when a material is confined substantially in one dimension. Quantum confinement effects mean that the density of states is no longer continuous, but step-like. The structure of FIG. 6(b) is known as a quantum well.

Confining the structure further in two dimensions, as shown in FIG. 6(c), we call the resulting structure a "quantum wire". We see a further change in the density of states function, and finally, confining the material in three dimensions, as seen in FIG. 6(d), we obtain what is known as a quantum dot. The available energy states are severely restricted discrete quantized (delta-shaped) energy states. The phenomena illustrated in FIG. 6 are well known in the field of semiconductor physics, for example as explained in the textbook Physics of Semiconductor Devices, by Simon M. Sze, Kwok K. Ng John Wiley & Sons, Inc., New Jersey ISBN-13: 978-0-471-14323-9 (see page 61), which is incorporated by reference herein in its entirety.

In the scientific literature, Raman spectroscopy of nanostructures has been studied, for example nanowires or various semi-conductor materials. We refer for example to the following papers:

Faraci et al, "Modified Raman confinement model for Si nanocrystals", Phys. Rev. B 73, 033307 (2006)

Faraci et al, "Quantum size effects in Raman spectra of Si nanocrystals" J. Appl. Phys. 109, 074311 (2011).

Wang et al, "Raman spectral study of silicon nanowires: High-order scattering and phonon confinement effects", Phys. Rev. B 61 (24), 16827 (2000).

Zhao et al, "Quantum Confinement and Electronic Properties of Silicon Nanowires" Phys. Rev. Lett. 92, 236805 (2004). These are all incorporated by reference herein in their entireties.

Figure 7:
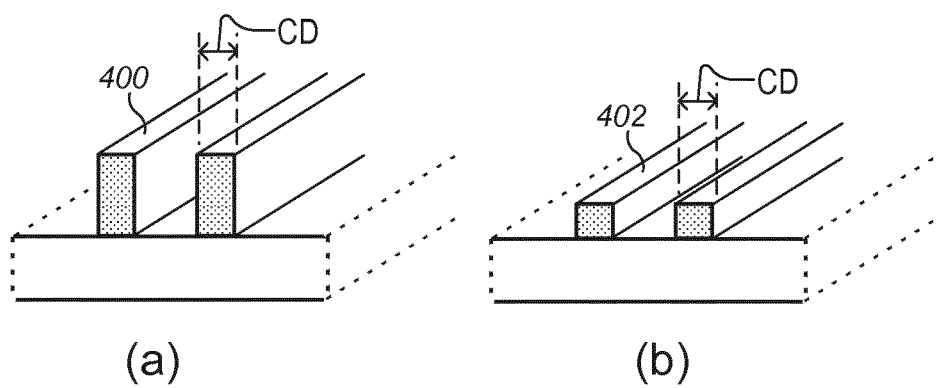
FIG. 7 illustrates structures formed by a lithographic process, illustrating different degrees of spatial confinement.

FIG. 7 illustrates structures that may be formed from semi-conductor or other materials in the manufacture of semi-conductor devices. Structures 400 are elongate and have a certain height. If their width is small enough, they will behave in some respects as Quantum wells. Similar structures 402 with a lower height may perform as Quantum wires, by analogy with structures seen in FIG. 6. Similar structures confined in three dimension shown at 412 can behave as quantum dots. Various other forms of structure can be envisaged, such as quantum dashes, having finite size in the 2D plane but shorter in one direction. Thus, a shortened quantum wire. It is likely in practice that product-like structures are dash shaped. They may also be arranged at different angles, not aligned with the X or Y axis.

A generic relationship between the Raman shift and peak broadening on the one hand, and dimensional characteristics of the target structure on the other, has been both observed in practice, and calculated by theoretical models. The present application proposes to exploit this observation use the phenomena of altered shift and broadening of Raman spectra to measure dimensional properties of very small structures. In particular, it has been recognized that, while conventional scatterometry techniques will struggle to recognize dimensional features as structures become smaller and smaller, the strength of the shifting and peak broadening phenomena caused by dimensional confinement increases below this range. Thus the new technique offers the prospect of an inspection apparatus that is able to make measurements well below 20 nm, without resorting to SEM or AFM techniques. Further, while quantum confinement effects on electrons and holes have been studied in detail and applied in many different types of electronic device, it is recognized that similar quantum effects arise in the energy states associated with vibrations of molecules and crystalline materials. These vibrational modes can be investigated by Raman spectroscopy in all types of materials. For silicon nanostructures, for example, the phonon confinement length is approximately 22 nm. This confirms that Raman spectroscopy be an effective method for measurement of dimensional characteristics of structures with dimensions below this length.

As will be explained shortly, a generic relationship between the Raman shift and a peak broadening and dimensional characteristics of the target structure has been both observed in practice, and calculated by theoretical models. The origin of this relationship lies in the fact that spatial confinement introduces quantum effects that restrict the availability of energy states within the material, whether they be vibrational modes or excitons. However, the practical use of the relationships for measurement of dimensional characteristics does not depend on any perfect theoretical model or quantitative data: usable measurements can be obtained simply by calibration of what is observed against known targets.

In Wang et al (2000), the Raman spectra of silicon nanowires of different dimensions are studied, both by measurement and by modeling. This study clearly indicates the sensitivity of the Raman spectrum to reduced feature size. The Raman peaks are seen to have large shifts, and become (i) less red shifted and (ii) broadened as the silicon nanostructure becomes smaller.

Faraci et al (2006, 2011) provide theoretical models that support the observed shift and broadening of Raman peaks as silicon nanostructures reduce in size. FIG. 5, mentioned above, is based on a figure from Faraci (2006) and depicts calculated Raman spectra for quantum dots of size 100 nm, 3 nm and 2 nm. The spectra are normalized to the same height as one another, taken to equal unity. Their line widths are measured at the half maximum intensity, as shown in FIG. 5. Faraci et al also present graphs that depict the behavior of Raman shift and FWHM as a function of feature size. Those graphs show the systematic influence of increasing phonon confinement. as feature size decreases. At sizes of ~5 nm and below, exciton confinement may also be playing a role.

Zhao et al (2004) confirms that nanometer-scale structures show quantum confinement of the exciton. For silicon nanowires, it is found that the exciton confinement length is approximately 5 nm. Confinement below this length leads to an increase of the exciton band gap energy, resulting in a shift of the exciton energy. Due to its influence in the Raman spectrum, this shift gives rise to a shift in the position and broadness of Raman spectral peaks, that can in turn be used as a measure of the nanostructure dimensions.

While the studies above have referred to silicon as a material of interest, the phenomena of quantum confinement, and Raman spectroscopy generally, are by no means limited to silicon or similar semiconductor materials. Rather, the techniques introduced herein can be applied to other semi-conductor materials, composite materials such as silicon nitride, and, notably, organic materials such as are used in lithographic processes as resist materials.

Figure 8:
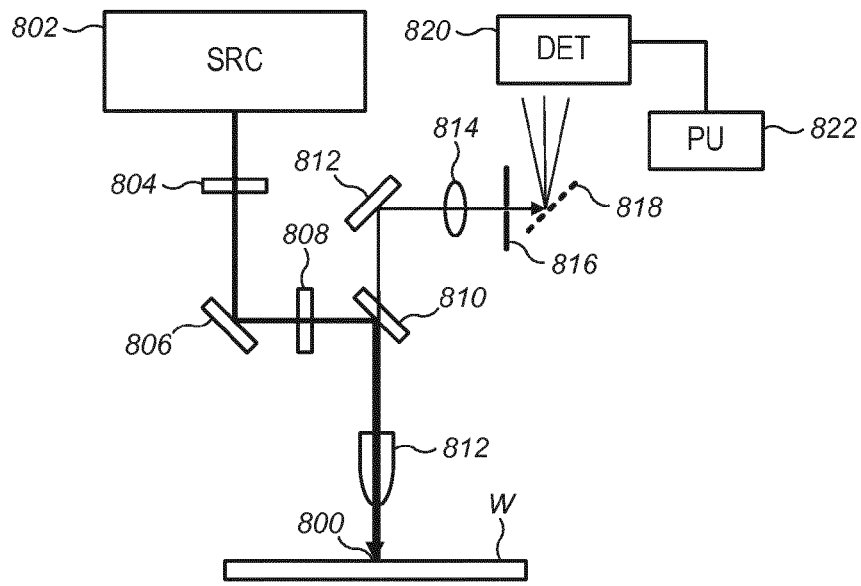
FIG. 8 is a schematic diagram of a practical instrument for applying Raman spectroscopy to the measurement of dimensions of structures formed on a substrate.

FIG. 8 illustrates the principal components of a practical inspection apparatus for using Raman spectroscopy to determine dimensional characteristics of a target structure. Target 800 may be formed on a substrate W that has been patterned and processed using the lithographic apparatus of FIG. 1 and the cluster of processing tools described above with reference to FIG. 2. The inspection apparatus comprises a source 802 of excitation radiation, a bandpass filter 804, a mirror 806, a polarizer 808, a beam splitter 810 and an objective lens 812. Target 800 may be mounted below the objective lens on a substrate table similar to the substrate table WTa in the lithographic apparatus. On the detection side, a mirror 812 is arranged behind the beam splitter 810, with a lens 814 and pin hole 816 leading to a spectroscopic grating 818. A detector 820 is arranged to receive a spectrum of radiation 821 from grating 818, and deliver spectral information to processing unit 822.

In operation, a monochromatic polarized beam of radiation is generated by source 802, bandpass filter 804 and polarizer 808. Filter 804 is provided to "clean up" the laser spectral output, so that only the desired wavelength is present. The resulting radiation forms the excitation beam 830 for the Raman spectroscopy, and is delivered via beam splitter 810 and objective 812 onto the structure 800 being examined. Scattered radiation returns through the same objective lens 812 to beam splitter 810. The beam splitter in this example has the form of a notch filter or dichroic mirror, so that radiation of the same wavelength as the excitation beam 830 cannot pass to mirror 812. Consequently, only the Raman-shifted radiation reaches the spectrometer that is formed by lens 814, pinhole 816, grating 818 and detector 820. Signals passed by the detector to processing unit 822 therefore represent the Raman spectrum of the target 800.

In an embodiment where the excitation radiation can have different wavelengths, an appropriate filter or dichroic mirror should be provided for the wavelength currently in use. This can be implemented simply by a filter wheel with different filters. The same applies to the filter 804 provided at the source side to "clean-up" the laser spectral output.

While FIG. 8 shows one example apparatus, numerous variations are possible. The source 802 may be a single or multi-wavelength laser, or a continuum laser (CW and pulsed lasers are possible, see an earlier remark). It may operate in continuous wave mode or pulsed mode, or some hybrid of the two. Polarizer 808 may be fixed in orientation, or may be adjustable, so as to alter the incident polarization to suit different targets. Of course the target and/or the apparatus may also be rotatable relative to one another, according to how they are mounted. Target 800 may also be rotatable, according to how they are mounted. Curved mirrors can be used for focusing radiation, in place of one or more of the lenses. This may be of particular interest if the waveband of interest is in the ultra-violet range.

Yet further modifications are possible at the detection side, detection arrangement 820 may comprise a single detector or multiple detectors. Typically an elongate pixel array will be provided for capturing the spectrum of radiation that has spread by the action of grating 818. Pinhole 816 may be a slit, so as to maximize the use of radiation, without blurring the spectrum. Since the spectral resolution required to resolve the features of a Raman spectrum is very fine, the path length from grating 818 to detector 820 may be much longer than indicated in this non-scale diagram. A path length from grating to detector may be for example 0.5 meter or 1 meter long. Such a long optical path can be folded by use of mirrors, to provide a more compact apparatus.

Figure 9:
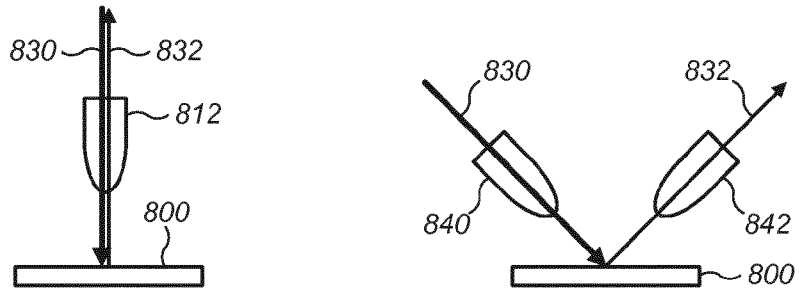
FIG. 9 (*a*) to (*e*) illustrates variations (*a*) to (*e*) in the construction of an instrument as seen in FIG. 8, in which variations (*c*) to (*e*) include a source of pump radiation source.
Figure 9:
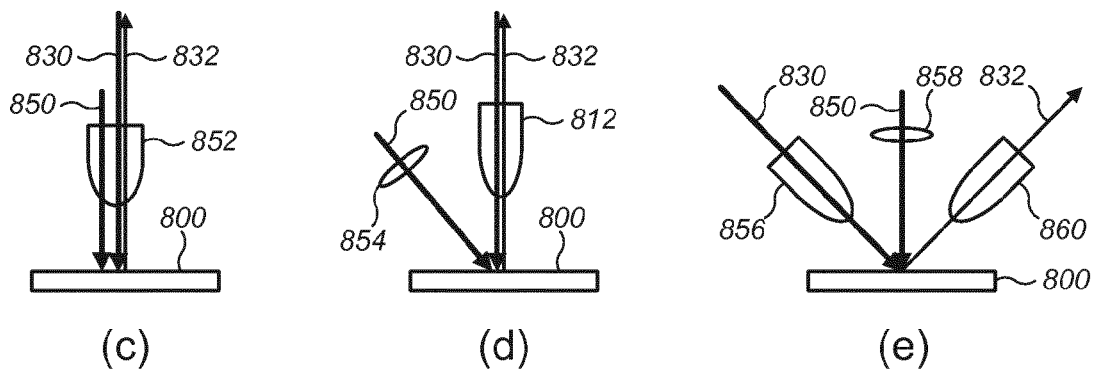

Referring to FIG. 9, various alternative configurations of the apparatus layout are possible, without changing the basic optical configuration and principles of operation. At FIG. 9(*a*) we see represented the arrangement of FIG. 8, where a single objective lens 812 carries both the excitation beam 830 and the scattered beam 832(*b*), a different arrangement is seen whereby the excitation beam 830 and the scattered beam 832 are processed through separate objective lenses are 840 and 842 respectively. The illumination of the target may be by normal incidence or by oblique incidence.

FIG. 9 (*c*), (*d*)and (*e*) show alternative configurations including also a pump laser, corresponding to the pump source 122 seen in FIG. 3. The pump source is not shown explicitly in FIG. 9, but the pumping radiation 850 is shown schematically. In pumped Raman spectroscopy, the excitation beam 830 is often referred to also as the "probe" beam, to distinguish it from the pump beam. In FIG. 9(*c*) a single objective lens 852 is responsible for delivering the pumping and probe radiation, as well as receiving the scattered radiation 832. In FIG. 9(*d*) the arrangement is the same as in FIG. 8 and FIG. 9(*a*), with the addition of a separate objective lens 854 for delivering the pumping radiation. Finally, in FIG. 9(*e*) we see three separate lenses with three beams, namely an objective 856 for delivering the excitation beam, lens 858 for delivering the pumping beam and objective lens 860 for collecting the scattered radiation 832.

It should be noted that, although FIGS. 9(*b*), (*d*) and (*e*) show a wide angle of divergence between the beams entering through the various lenses, in practice attention must be paid to proper alignment of the wave vector of the different radiation beams. That is to say, if the wave vector of the pump radiation is significantly misaligned with that of the excitation radiation, the energy states excited within the sample by the pump beam may not be to interact with the excitation (probe) beam 830 so as to enhance the Raman signal. The only effect of the pumping laser in that case would be to heat the sample. Therefore, the skilled person will understand that the beams, even if they are delivered by separate optical systems, may be much more closely aligned than is illustrated in the schematic diagrams.

Additionally, when using a pump laser (or two excitation sources), both lasers should normally also be synchronized in time. Thus, a control loop (not shown) would be included in the apparatus to control the timing of laser pulses generated by the two sources. Synchronization could also be done by including a form of "delay line" in the optical path, instead of a control that directly drives the lasers.

With these various components in suitable configurations, the skilled person will be able to apply many specific varieties of Raman spectroscopy that are known in the art. These include: Kerr-Gated Raman spectroscopy; Fourier-transform Coherent Anti-Stokes Raman Spectroscopy (CARS); Hyper Raman spectroscopy; Surface Enhanced (resonance) Raman Spectroscopy (SE(R)RS); Stimulated Raman scattering (SRS)—SRS four-wave mixing; Time-resolved Raman spectroscopy. SRS and CARS are coherent Raman scattering techniques that allow the enhancement of weak Raman signals by means of nonlinear excitation. More details of all these techniques can be found in the literature. Irrespective of the technique used, it may be expected that spatial confinement of phonons and other quasi-particles will allow dimensional characteristics of a structure to be detected by their effect on the Raman spectrum.

Figure 10:
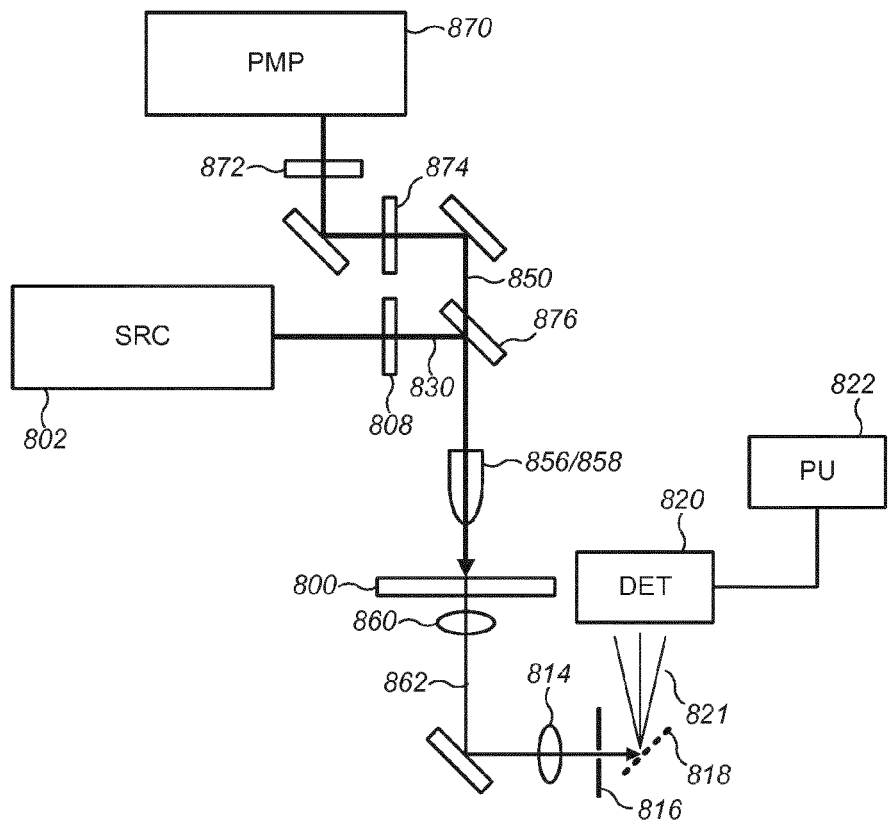
FIG. 10 illustrates another variation in the construction of the instrument, where forward scattered radiation is detected.

FIG. 10 illustrates a further option, in which the Raman radiation is scattered forward (i.e. transmitted through the sample) instead of being reflected backwards as illustrated in the previous examples. In the FIG. 10 arrangement, parts are numbered similarly as in FIG. 9(*e*), with the source and optics for the pump and excitation beams (pump and probe beam in other words) being located on the upper side of the target 800, and the optics and detection arrangement for Raman shifted light being located behind the target. Of course, in practice, the orientation of the target is irrelevant, and terms such as top, bottom, front and back can be interpreted interchangeably.

Pump source 870 is shown, which may be a single or multiple wavelength (tunable) laser or a continuum laser for supplying radiation in a wavelength range suitable to excite the desired energy state within target 800. The beam path for the pumping laser beam 850 includes a band pass filter 872 and a polarizer 874. The pumping beam 850 and the excitation (probe) beam 830 are combined in a dichroic mirror 876 and delivered to the target through a common objective lens 856/858. The dichroic mirror 876 is used as the bandpass filter (804 in FIG. 8) to select the desired excitation wavelength to be reflected into the objective lens, while mirror will also be transparent for the pumping radiation. Hereby, both lasers can be aligned such that their paths overlap and enter the common objective 856/858

Collection optics for the Raman scattered light 862 comprises a lens 860 at the back side of the target 800. Of course, this embodiment supposes that the Raman signal will be scattered in the forward direction of the excitation beam and be detectable at the back side of the substrate. The apparatus in this variation may be configured for example to implement CARS, as mentioned above. Depending on the wavelengths used and the material of the substrate, this embodiment may benefit from the excitation radiation being suppressed by absorption in the substrate or in a particular material layer on the substrate.

Figure 11:
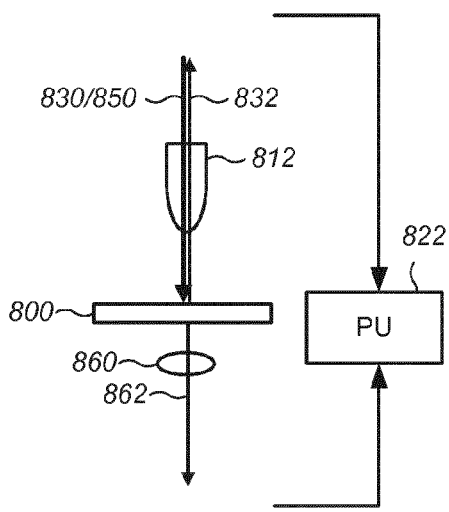
FIG. 11 illustrates another variation in the construction of the instrument, where both backward and forward scattered radiation are detected.

FIG. 11 shows an alternative configuration in which Raman radiation is detected that has been scattered forward and reflected backwards. That is to say, elements of the examples of FIGS. 9 and 10 can be combined in a single instrument, without changing the basic optical configuration and principles of operation. In the arrangement of FIG. 11, parts are numbered similarly as in FIGS. 10 with scattered beam 832 representing the backward scattered Raman radiation and scattered beam 862 representing the forward scattered Raman radiation. The source and optics for the excitation beam 830 and pump beam 850 (if provided) are not shown in FIG. 11, are located on the upper side of target 800, for example, as disclosed in FIGS. 9 (*c*) and 10. However, optics and detection arrangements for Raman shifted light are located on both the upper side and lower side of target 800, not only one side or the other. For example, the backward Raman scattering may be detected by optics and detection arrangement similar to optics and detection arrangement of FIG. 8. The forward Raman scattering may be detected, for example, by optics and detection arrangement similar to optics and detection arrangement of FIG. 10. Processing unit 822 receives signals from detectors of both the forward and backward radiation. Depending on the particular target, and on the dimensional characteristic under investigation, processing unit 822 may select between forward and backward signals, or use a combination of forward and backward signals, to obtain an optimum measurement of the dimensional characteristic.

The orientation of the target is irrelevant, and terms such as top, bottom, front and back can be interpreted interchangeably. Skilled person will be able to adapt the apparatus layout to detect forward and backward scattered Raman radiations. Alternative configurations may include a pump laser and separate objective lens for delivering probe and pumping radiation, as disclosed in FIG. 9.

Figure 12:
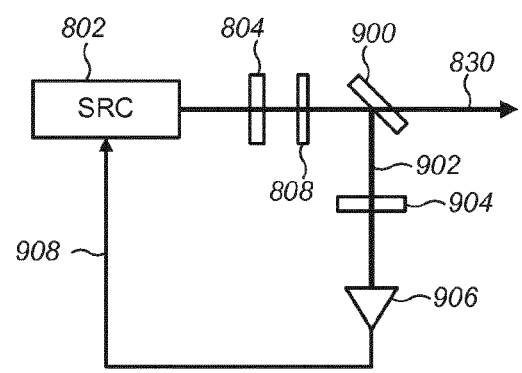
FIGS. 12 illustrates a radiation source arrangement including feedback control, for use in the apparatuses of FIGS. 8 to 10.

FIG. 12 illustrates another variation that may be applied in the above embodiments, to provide real-time feedback control of the excitation laser. In FIG. 12, a beam splitter 900 taps off a small portion 902 of the excitation beam, which is passed through a filter 904 and to a detector 906, detector 906 compares the signal intensity with a desired level, and generates a feedback control signal 908 which is supplied to control a source 802. The second filter 904 is a neutral density filter to avoid over exposure of the detector.

Figure 13A:
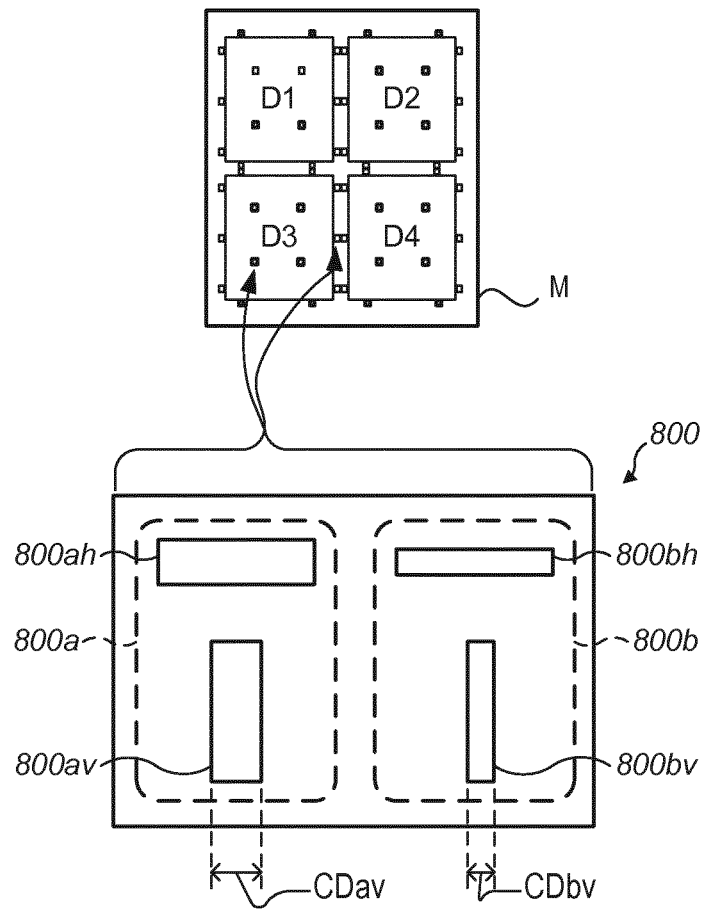
FIGS. 13 (*a*) and (*b*) show the form of example target structures for use with the apparatus of FIGS. 8 to 10 in monitoring performance of a lithographic process.
Figure 13B:
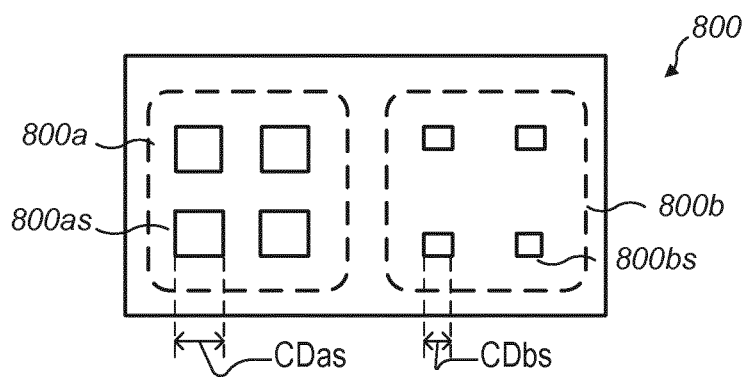

FIG. 13 (*a*) shows schematically the overall layout of a patterning device M and metrology targets for use with the inspection apparatus of FIGS. 8 to 11. As is well known, patterning device (mask) M may contain a single device pattern, or an array of device patterns if the field of the lithographic apparatus is large enough to accommodate them. It is assumed for the sake of example that the patterning device is an optical lithography mask, but it might also be an imprint device, for example. In other systems, a physical mask may not be used at all, and the patterning device may be programmable, for example using deformable mirror devices or direct-write techniques. The example in FIG. 13 (*a*) shows four device areas labeled D1 to D4. Scribe lane targets are placed adjacent these device pattern areas and between them. On the finished substrate, such as a semiconductor device, the substrate W will be diced into individual devices by cutting along these scribe lanes, so that the presence of the targets does not reduce the area available for functional device patterns. Where targets are small in comparison with conventional metrology targets, they may also be deployed within the device area, to allow closer monitoring of lithography and process performance across the substrate. Some targets of this type are shown in device areas D1-D4.

While FIG. 13 (*a*) shows the patterning device M, the same pattern is reproduced on the substrate W after the lithographic process, and consequently this the description applies to the substrate W as well as the patterning device. For manufacturing a real product on substrate W, many different device layers may be applied in sequence, using a corresponding sequence of patterning devices forming a complete mask set.

The lower part of FIG. 13 (*a*) shows a target 800 in more detail. The target is divided into two target areas 800*a* and 800*b*. Within each area, there are one or more horizontally oriented structures 800*ah*, 800*bh* and one or more vertically oriented structures 800*av*, 800*bv*. The structures in area 800*a* are of relatively larger dimensions than the actual product features whose critical dimension is of interest, and will be used for calibration of the dimensional metrology based on Raman spectroscopy. The structures in area 800*b* are formed to be as close as possible in all characteristics to devices structures of interest within the device areas D1-D4. The structures in calibration area 800*a* are formed so as to be as close as possible to the device structures in all characteristics except size. There may be a single structure of each type and orientation, as illustrated, or there may be an array of structures, which may be arranged periodically so as to make a grating (not shown). A grating structure is not required, however, unlike in scatterometry where predictable diffraction is the operating principle. A point to note, when designing targets in the form of a grating, is that excitons in neighboring lines or dots may be influenced by one another so as to change behavior, relative to a single, isolated structure.

As an example, while the structures in area 800*b* may have a dimension of 10 nm, the structures in calibration area 800*a* may have a dimension of 50 or 100 nm. The dimension of the calibration structure is a matter for careful design choice. It should be as close as possible to that of the device structure, without experiencing the same quantum confinement effects. Otherwise, differences in processing of the calibration structures may cause them to have different characteristics other than size as well. For example, structures formed by processes such as etching, and chemical-mechanical polishing may have many differences in layer height, edge roughness, material stresses, doping, and the like, if they are very different in dimension. All of these parameters can have a dramatic effect on the Raman spectrum, which would interfere with the desired measurement of CD. As examples based on common types of materials, embodiments of the invention may have calibration structures with critical dimension greater than 25 nm, say, while device-like structures have a dimension less than 20 nm for example less than 10 nm.

Providing horizontally and vertically oriented structures allows the influence of processing such structures to be measured. Also, it allows measurement using different polarizations of radiation without rotating the target or the polarizer in the inspection apparatus. In a practical embodiment, there may be different types of device structures and more than one area 800*b* may be provided. For example, even with the same nominal CD, there may be line structures and dot structures (such as for forming contact holes (vias)).

FIG. 13(*b*) illustrates a second example target, in which dot-like features are formed, for example to resemble contact holes in the device pattern. Again, calibration structures are provided in a calibration area 800*a*, and device-like structures are provided in area 800*b*. In this example each area 800*a*, 800*b* contains arrays of structures 800*as*, 800*bs* having a dot-like form, and having critical dimensions CDas and CDbs respectively. Further variations would include "quantum dash" features shorter and/or longer than those shown in FIG. 13(*a*).

While the features in FIGS. 13(*a*) and (*b*) are shown oriented to the X and Y directions of the substrate coordinate plane, real device structures may not be so oriented. For example, certain layers in DRAM (dynamic random access memory) devices of the "6f2" design have features aligned at an oblique angle, that is to say aligned neither with X or Y axes. For metrology on substrates carrying these device layers, the metrology targets for Raman spectroscopy can be provided with lines and/or dots arrayed at angles corresponding to the alignment of the product features.

Similarly, for calibration purposes, there may be more than one calibration area 800*a*. Calibration structures of different dimensions may be provided as well, to provide additional points on a calibration curve. It may be desirable for example to provide calibration structures different dimensions, for example where phonon confinement effects and exciton confinement effects come into play at different scales, and/or where confinement effects come into play at different scales in different materials. In principle, a calibration structure does not need to be provided (or measured) for every device-like structure, but measurement accuracy depends on eliminating as far as possible process and material variables, and many of these variables are known to vary with position across a substrate. The calibration structures also serve to calibrate the measurement against variations in intensity of the excitation beam. In principle, a calibration structure could be smaller than the device-like structure, if its dimensions are well known. In most applications, however, it will be the smaller structures whose dimensions are known with less certainty, and the calibration structures will be larger.

The targets illustrated in FIG. 13 and described above are consequently only a few examples of targets usable in embodiments of the invention, and many variations can be envisaged. Moreover, the invention is not limited to measuring patterns formed on semiconductor devices but can be applied to a variety of structures. Also, it may be expected that targets for many different purposes may be provided alongside the target 800 on a real substrate. A typical device manufacturing process will use alignment marks, overlay measurement marks and the like at various positions. Further, different target types may be provided on the masks for different layers. For example, while the present Raman metrology targets may be required on some critical layers, other layers may have relaxed dimensional tolerances an may use conventional scatterometry targets.

Figure 14:
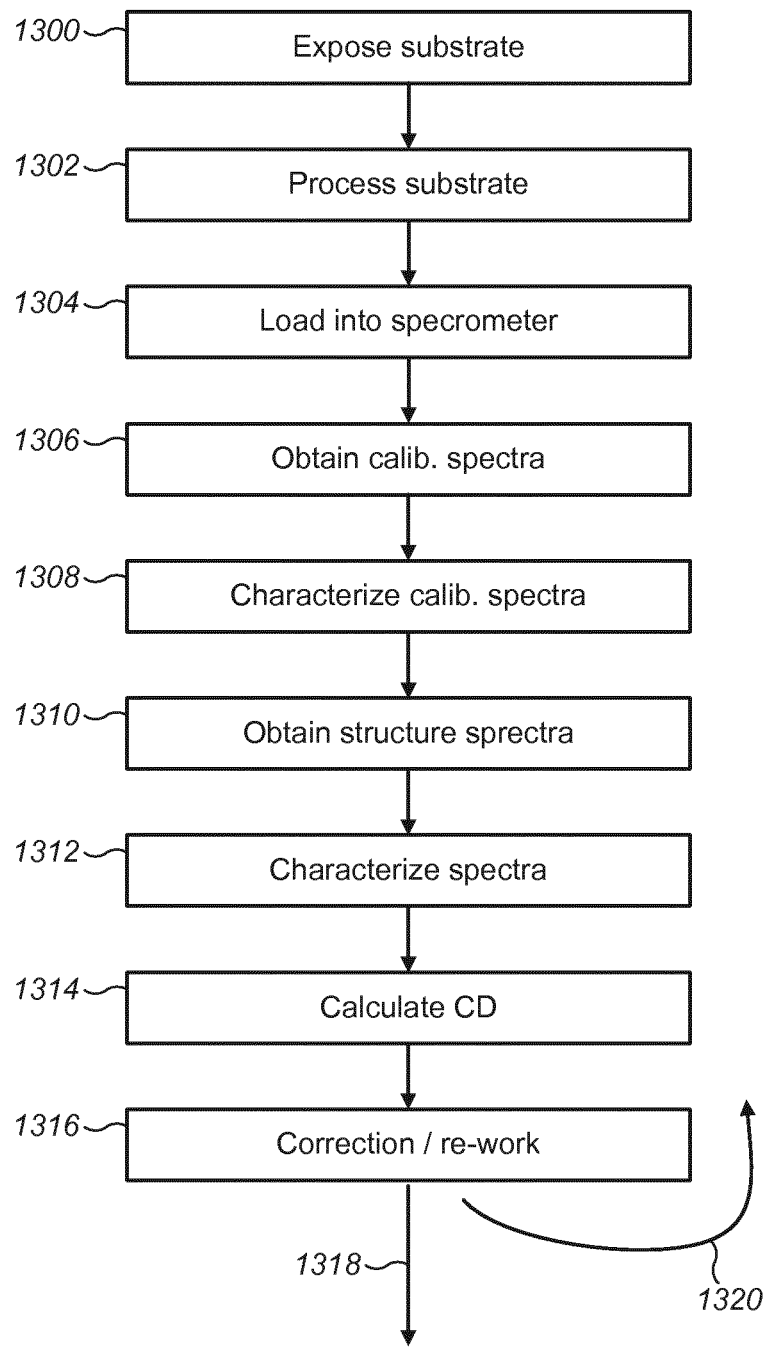
FIG. 14 is a flowchart of an example device manufacturing method including inspection of microscopic structures according to an embodiment of the invention.

FIG. 14 is a flowchart summarizing one possible method of measuring dimensional characteristics of a target structure using principles of Raman spectroscopy and quantum confinement. The method forms part of a device manufacturing method in which, for example, a set of patterning devices M of the type shown in FIG. 12 are used to create a complex semiconductor device. The flowchart shows processing for essentially one layer, it being understood that the steps will be repeated, with appropriate modifications, to build up the device structure layer-by-layer.

At step 1300, a device pattern including target structures 800 is applied to a substrate using a lithographic apparatus of the type shown in FIG. 1. (In fact, for structures of the small dimensions mentioned here, it may be that an EUV lithographic apparatus or other technique is applied. The difference is not material to the inspection apparatus and method.) At 1302, the pattern including the target structures 800 is developed in the resist, and may be subject to various further processing steps before the CD measurement. The structures to be measured may in fact be ones produced by so-called double- or triple-patterning, so that several lithographic patterning steps and/or other processing steps are required to produce even a single set of lines in a single device layer.

At 1304, the substrate is loaded into the inspection apparatus of (for example) FIG. 8. In some embodiments, the inspection apparatus will be a separate unit from the lithographic apparatus, and may be associated with one or more litho clusters. In other embodiments, the Raman spectroscopy apparatus may be integrated into the lithographic apparatus, and used for example during the pre-exposure metrology phase (alignment). In such a case, the loading in step 1304 is effectively the loading of the substrate into the lithographic apparatus prior to the application of another patterned layer. Inspection using the apparatus may be performed on all substrates, or only a sample. Other substrates, or other layers on the same substrate, may be not inspected, or may be inspected using a conventional scatterometer or other means. The same substrate may of course be subject to other types of inspection, besides the one described here.

At 1306, the apparatus locates a target 800 and obtains one or more Raman spectra from one or more of the structures within the calibration area 800*a*, according to a programmed inspection recipe. Multiple spectra can be obtained using the same or different excitation wavelengths and the same or different polarizations, for example. At 1308 certain peaks in the spectrum or spectra may be identified and characterized as to their peak wavelength (frequency or wavenumber) and their width (FWHM). The peaks of interest may be specified in the inspection recipe.

At 1310 the apparatus obtains one or more Raman spectra from one or more of the structures within the target area 800*b*, under the same conditions or wavelength, polarization etc. as were used in step 1306. At 1312, peaks in the measured spectrum or spectra are identified and characterized as to their peak wavelength and width, by processing unit 822. The inspection recipe ensures that the spectra and peaks selected for measurement and characterization are the same as for the calibration structures.

At 1314, by comparing the measured characteristics of one or more peaks in the spectra obtained in steps 1306 and 1310, the processing unit 822 calculates CD or other dimensional parameters of the target structure in area 800*b*. This is output to be used as a measurement of the CD of device structures. The calculation can be based entirely on empirically obtained relationships, on theoretical models, or on a combination of both. In this way, the utility of the method is not dependent on the complete and accurate understanding of the underlying physical phenomena.

It goes without saying that the steps 1306-1314 can be repeated for different targets located across the substrate to obtain a map of said dimensional characteristic as it varies across the substrate. In doing this, it is a matter of design choice whether any or all of the analysis and calculation steps 1308, 1312 and 1314 are performed concurrently with the obtaining steps 1306, 1308, or only after all the data have been collected.

At 1316, optionally an action may be triggered by a CD measurement (or group of measurements) exceeding certain tolerances defined in the inspection recipe or in a control program of the litho cluster or lithographic apparatus. A range of actions may be envisaged, depending which thresholds have been exceeded. Thresholds for one layer or device type may be different than for others. One action where the measured CD is outside a functional tolerance would be to divert the substrate for re-work, or for scrapping. Although it is costly to re-work or scrap substrates, it is also costly to occupy the litho cluster processing subsequent layers on a substrate that is already defective in one critical layer. Another type of action, where the measured CD is within a functional tolerance, would be to feed the CD measurement and/or a suggested correction into a process control system, so that parameters of the lithographic process can be adjusted to improve the CD for subsequent substrates.

Depending which particular product layer is being patterned, the processing either concludes at 1318 or returns at 1320 for further steps of coating, exposing, etching and so forth. When the process has concluded, the substrate proceeds to testing, dicing and packaging steps, to deliver the finished semiconductor product.

Although specific reference may be made in this text to the use of lithographic apparatus in the manufacture of ICs, it should be understood that the lithographic and metrology apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, and use of the terms "wafer" or "die" herein may be considered as synonymous with the more general terms "substrate" or "target portion", respectively.

Although specific reference may have been made above to the use of embodiments of the present invention in the context of optical lithography, as already mentioned, is not limited to optical lithography. In imprint lithography, for example, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured. The pattern to be applied to the substrate need not be physically present on a mask-like patterning device. Another known alternative is to provide a programmable patterning device and/or to use a so-called direct write method. The term "patterning device" should therefore be interpreted as encompassing also devices in which the pattern to be applied is defined by stored digital data.

The lithographic apparatus of Figure above may be designed to operate using radiation at UV wavelengths, the designs can be adapted by the skilled person to use a different or wider range of wavelengths, if desired. The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components. For EUV wavelengths in particular, the projection system PS of FIG. 1 will be forms of reflective elements.

While specific embodiments of the present invention have been described above, it will be appreciated that the present invention may be practiced otherwise than as described. For example, the present invention, particularly with regard to the control of the measurement process and processing of the results for calibration and measurement, may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that yet further modifications may be made to the present invention as described without departing from the spirit and scope of the claims set out below.

The invention claimed is:

1. A method of inspecting a target structure, the method comprising:
    directing radiation with a first wavelength at the target structure;
    receiving radiation scattered by the target structure and forming a spectrum of the scattered radiation so as to distinguish one or more spectral components in the spectrum having wavelengths different from the first wavelength due to inelastic scattering by the target structure; and
    calculating a dimensional characteristic of the target structure based on characteristics of the one or more spectral components, wherein the calculating comprises comparing the characteristics of the one or more spectral components obtained from the target structure with characteristics of corresponding one or more spectral components obtained from a calibration structure, the target structure and the calibration structure being different in at least one dimension.

2. The method as claimed in claim 1, wherein the illumination and the receiving are performed through separate objective elements.

3. The method as claimed in claim 2, wherein at least part of the scattered radiation is received on a side of the target structure opposite to that of illumination optics configured to direct the radiation with the first wavelength at the target structure, thereby to receive forward scattered radiation.

4. The method as claimed in claim 3, wherein another part of the scattered radiation is received on a side of the target structure same as that of the illumination optics, thereby to receive forward and backward scattered radiation.

5. The method as claimed in claim 1, wherein the target and calibration structures having similar characteristics except the at least one dimension.

6. The method as claimed in claim 1, wherein the calibration structure has a critical dimension larger than a critical dimension of the target structure.

7. The method as claimed in claim 1, wherein the calculating is based at least partly on a broadening of one or more of the one or more spectral components.

8. The method as claimed in claim 1, wherein the characteristics of the one or more spectral components comprise peak wavelength and width of the one or more spectral components.

9. An inspection apparatus comprising:
    illumination optics configured to direct radiation with a first wavelength at a target structure;
    detection optics configured to receive radiation scattered by the target and for forming a spectrum of the scattered radiation;
    a detector configured to convert the spectrum into electrical signals; and
    a processor configured to calculate a dimensional characteristic of the target structure based on characteristics of one or more spectral components in the detected spectrum having wavelengths different from the first wavelength due to inelastic scattering, wherein the calculating comprises comparing the characteristics of the one or more spectral components obtained from the target structure with characteristics of corresponding one or more spectral components obtained from a calibration structure, the target structure and the calibration structure being different in at least one dimension.

10. The apparatus as claimed in claim 9, wherein the illumination optics and the detection optics comprise separate optical elements.

11. The apparatus as claimed in claim 10, wherein at least a part of the detection optics is located on a side of the target structure opposite to that of the illumination optics, thereby to receive forward scattered radiation.

12. The apparatus as claimed in claim 11, wherein parts of the detection optics are located on both sides of the target structure, thereby to detect forward and backward scattered radiation.

13. The apparatus as claimed in claim 9, wherein the target and calibration structure having similar characteristics except the at least one dimension.

14. The apparatus as claimed in claim 9, wherein the processor is configured to perform the calculation based at least partly on a broadening of one or more of the one or more spectral components.

15. A method of performing a lithographic process comprising:
    forming device structures and a target structure on a substrate by the lithographic process;
    measuring a dimensional characteristic of the target structure by:
        directing radiation with a first wavelength at the target structure,
        receiving radiation scattered by the target structure and forming a spectrum of the scattered radiation so as to distinguish one or more spectral components in the spectrum having wavelengths different from the first wavelength due to inelastic scattering by the target structure, and
        calculating the dimensional characteristic of the target structure based on characteristics of the one or more spectral components, wherein the calculating comprises comparing the characteristics of the one or more spectral components obtained from the target structure with characteristics of corresponding one or more spectral components obtained from a calibration structure, the target structure and the calibration structure being different in at least one dimension; and
    controlling subsequent processing of the measured substrate in accordance with the measured dimensional characteristic.

16. A method of inspecting a target structure, the method comprising:
    directing radiation with a first wavelength at the target structure;
    receiving radiation scattered by the target structure and forming a spectrum of the scattered radiation so as to distinguish one or more spectral components in the spectrum having wavelengths different from the first wavelength due to inelastic scattering by the target structure; and
    calculating a dimensional characteristic of the target structure based on characteristics of the spectral components, wherein the calculating is based, at least in part, on a broadening of one or more of the one or more spectral components.

17. An inspection apparatus, comprising:
    illumination optics configured to direct radiation with a first wavelength at a target structure;
    detection optics configured to receive radiation scattered by the target and for forming a spectrum of the scattered radiation;
    a detector configured to convert the spectrum into electrical signals; and
    a processor configured to calculate a dimensional characteristic of the target structure based on characteristics of one or more spectral components in the detected spectrum having wavelengths different from the first wavelength due to inelastic scattering, wherein the processor is configured to perform the calculating based, at least in part, on a broadening of one or more of the one or more spectral components.

* * * * *